United States Patent [19]

Sandlass et al.

[11] Patent Number: 5,767,402
[45] Date of Patent: Jun. 16, 1998

[54] MATERIAL TESTING SYSTEM HAVING DC BRUSHLESS LINEAR MOTOR

[75] Inventors: Gary S. Sandlass, Maple Plain; Larry G. Mosiman, Eden Prairie; Scott G. Johnson, Chaska; Douglas S. Morrissette, Plymouth, all of Minn.

[73] Assignee: MTS Systems Corporation, Eden Prairie, Minn.

[21] Appl. No.: 612,124

[22] Filed: Mar. 7, 1996

[51] Int. Cl.⁶ .................. G01B 7/16; G01L 1/00
[52] U.S. Cl. .......................... 73/779; 73/796
[58] Field of Search .............. 73/790, 779, 796, 73/774, 826, 853, 856

[56] References Cited

U.S. PATENT DOCUMENTS

| | | | |
|---|---|---|---|
| 3,369,390 | 2/1968 | Chu et al. | 73/15.6 |
| 3,813,919 | 6/1974 | Taniguchi et al. | 73/15.6 |
| 3,899,699 | 8/1975 | Griffing | 310/13 |
| 4,096,741 | 6/1978 | Sternstein | 73/817 |
| 4,099,106 | 7/1978 | Nikaido | 318/115 |
| 4,234,831 | 11/1980 | Kemmer et al. | 318/115 |
| 4,335,615 | 6/1982 | Kalfa et al. | 73/799 |
| 4,456,934 | 6/1984 | Wedman et al. | 360/78 |
| 4,500,827 | 2/1985 | Merritt et al. | 322/3 |
| 4,535,260 | 8/1985 | Pritchard et al. | 310/12 |
| 4,562,743 | 1/1986 | Bonine | 73/828 |
| 4,841,779 | 6/1989 | Mitsuhashi et al. | 73/826 |
| 4,870,306 | 9/1989 | Petersen | 310/12 |
| 4,912,746 | 3/1990 | Oishi | 310/12 |
| 4,945,268 | 7/1990 | Nihei et al. | 310/12 |
| 4,998,825 | 3/1991 | Hublikar et al. | 73/826 |
| 5,047,676 | 9/1991 | Ichikawa | 310/12 |
| 5,075,583 | 12/1991 | Sakagami et al. | 310/12 |
| 5,079,458 | 1/1992 | Schuster | 310/12 |
| 5,091,665 | 2/1992 | Kelly | 310/12 |
| 5,146,123 | 9/1992 | Yarr | 310/15 |
| 5,179,306 | 1/1993 | Nasar | 310/14 |
| 5,188,456 | 2/1993 | Burke et al. | 374/50 |
| 5,389,844 | 2/1995 | Yarr et al. | 310/15 |
| 5,424,952 | 6/1995 | Bluen et al. | 310/28 |
| 5,434,549 | 7/1995 | Hirabayashi et al. | 335/229 |
| 5,438,227 | 8/1995 | Satomi | 310/14 |
| 5,440,183 | 8/1995 | Denne | 310/12 |
| 5,511,431 | 4/1996 | Hinton | 73/806 |

OTHER PUBLICATIONS

Brochure: "New Way® Porous Carbon Air Bearings and Precision Machine Components". Devitt Machinery Co., Aston, PA, no date.

Trilogy Systems Corp., "Linear Motors & Motion Systems". pp. 2–5, 12–13.

"High–Force Actuator Operates Hydraulic Valve", Mark Gottschalk, *Design News*, Nov. 15, 1993, pp. 89–90.

"Special Linear Motor Issue —Positioning Market Is Moving Fast", *Anonews –The Technology Newsletter of the Anorad Corporation*, vol. 12, No. 5, Dec. 1993.

"Linear Motion Technology Update –Better motion control",Leslie Langnau, *Power Transmission Design*,Apr. 1995, pp. 55–57.

Primary Examiner—Elizabeth L. Dougherty
Assistant Examiner—Max H. Noori
Attorney, Agent, or Firm—Westman, Champlin & Kelly, P.A.

[57] ABSTRACT

A material testing machine includes a support structure and a DC brushless linear motor operable to develop a force along a reaction axis. The DC brushless linear motor includes a set of magnets disposed along a line on the support structure parallel to the reaction axis. An elongated member slidably guided by the support structure on the reaction axis includes a plurality of coils proximate the set of magnets. A controller selectively energizes the coils.

9 Claims, 5 Drawing Sheets

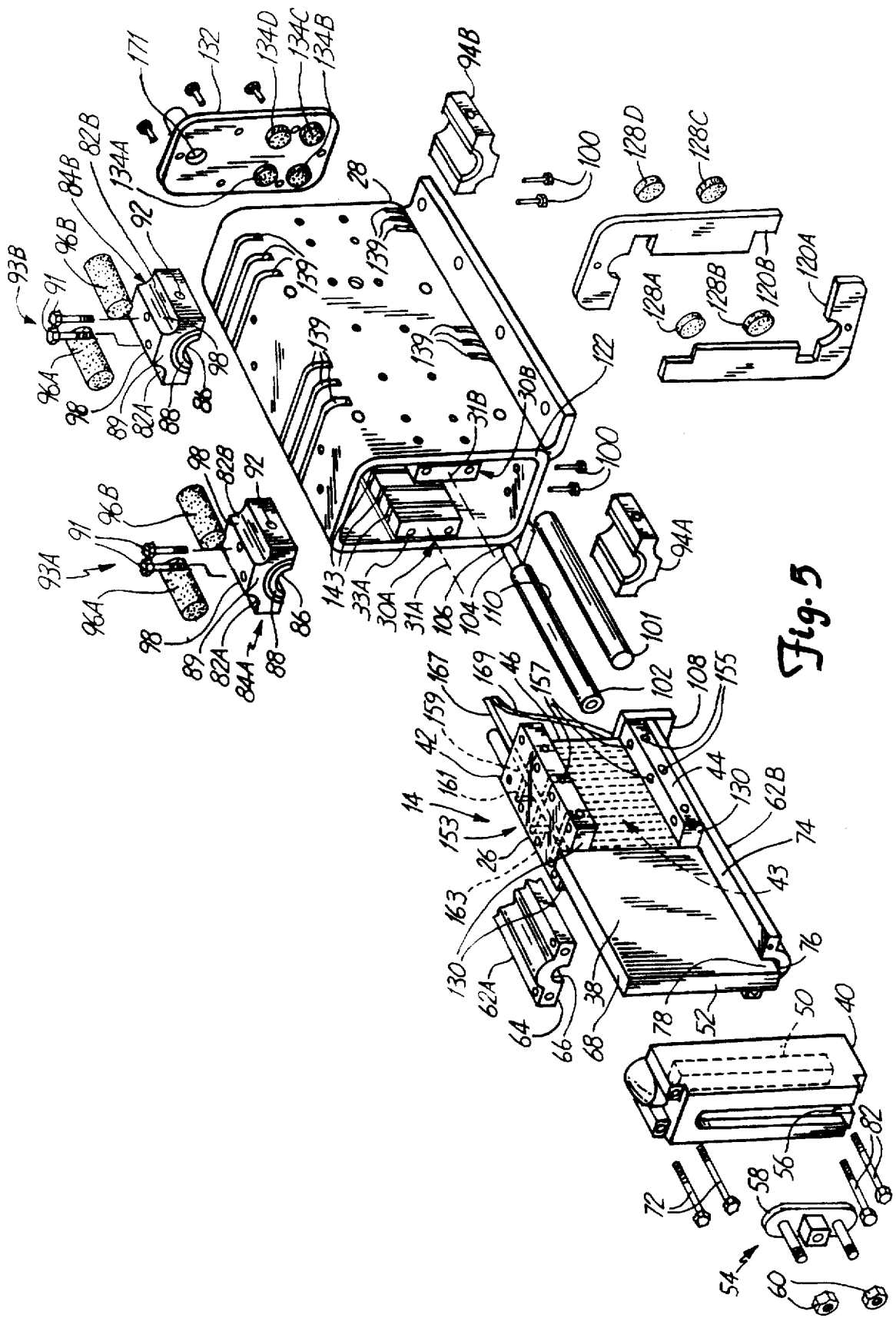

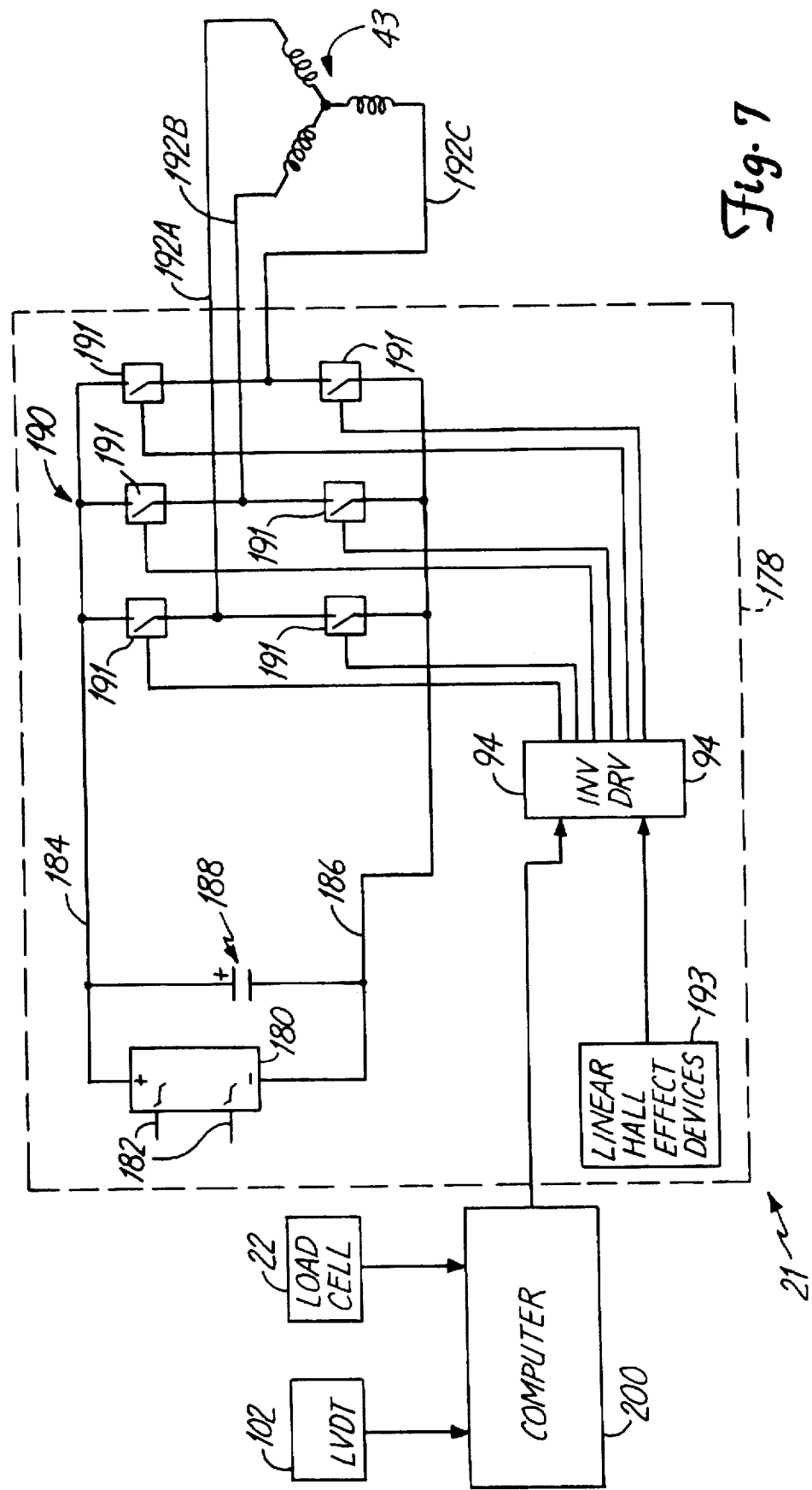

5,767,402

MATERIAL TESTING SYSTEM HAVING DC BRUSHLESS LINEAR MOTOR

BACKGROUND OF THE INVENTION

This invention is directed to an apparatus for applying stresses on materials by stretching and/or compressing the materials. More specifically, the present invention is related to an apparatus having an electromagnetic actuator to apply forces.

The physical testing of materials by taking a test specimen and applying tension and/or compressive loads using an actuator is well known. Commonly, hydraulic actuators have been employed to develop these forces. However, although hydraulic actuators can develop high forces, hydraulic actuators typically are just a part of a larger hydraulic system that requires other complicated devices such as accumulators, filters and pumps, which all must be maintained in order for the system to operate. Furthermore, being that the hydraulic system operates using pressurized fluid, there is always the risk of a fluid leak.

Electric motors have also been employed in actuators. In one application, linear motion is achieved by converting torque from a rotating electric motor through a ball screw assembly. A significant drawback of this assembly is the mechanical backlash that exists when displacement is reversed. In order to minimize backlash, preloaded fasteners must be used across the assembly. However, use of preloaded fasteners will introduce load dependent, non-linear friction.

U.S. Pat. No. 5,188,456 to Burke et al. disclose a fiber testing device having a linear step motor. The linear step motor includes a moving member and a stationary platen. The moving member includes two electromagnets and pole faces to concentrate magnetic flux developed by the electromagnets. Teeth of the pole faces are arranged so that only one set of teeth in each of the electromagnets can be aligned with corresponding teeth on the platen to provide discrete steps. The permanent magnet is disposed between the electromagnets. When a current is established in one of the field windings, the resulting magnetic field tends to reinforce the magnetic flux at one pole face and cancel it at the other. By selectively applying current, the moving member can be moved in one direction or the other. However, backlash due to bearing slop still exists since an axis of the test specimen to be tested is offset from an axis of force generation between the electromagnets of the moving member and the stationary platen.

SUMMARY OF THE INVENTION

A material testing machine includes a support structure and a DC brushless linear motor operable to develop a force along a reaction axis. The DC brushless linear motor includes a set of magnets disposed along a line on the support structure parallel to the reaction axis. An elongated member slidably guided by the support structure on the reaction axis includes a plurality of coils proximate the set of magnets. A controller selectively energizes the coils.

In one embodiment, the DC brushless linear motor further includes a second set of magnets disposed along a second line on the support structure parallel to the first line wherein the reaction axis is interposed between the first line and the second line. In this manner, electromagnetic forces are generated symmetrically about the reaction axis. The first guide assembly is operably connected between the support structure and the elongated member and has a first guide axis spaced-apart and parallel to the reaction axis. A second guide assembly is also operably connected between the support structure and the elongated member and has a second guide axis spaced-apart and parallel to the reaction axis. In a preferred embodiment, the first guide axis and the second guide axis are symmetrical to the reaction axis and are disposed in a common plane thereby yielding no backlash when displacement of the elongated member is reversed.

Another aspect of the present invention is a material testing machine comprising a support structure and a linear motor operable to develop a force along a reaction axis. The linear motor includes a first set of magnets disposed along a first line on the support structure parallel to the reaction axis and a second set of magnets disposed along a second line on the support structure parallel to the first line. The reaction axis is interposed between the first line and the second line. An elongated member is disposed on the reaction axis and has a plurality of coils proximate the first set of magnets and a second set of magnets. A controller selectively energizes the coils. By providing two sets of magnets on opposite sides of the reaction axis, electromagnetic forces generated to move the elongated member are balanced.

In another aspect of the present invention, a material testing machine includes a support structure and a linear motor operable to develop a force along a reaction axis. The linear motor includes a set of magnets disposed along a line on the support structure parallel to the reaction axis. An elongated member is slidably guided by the support structure on the reaction axis and has a plurality of coils proximate the set of magnets. A controller selectively energizes the coils. A first guide assembly is operably joined to the elongated member and the support structure. The second guide assembly is operably joined to the elongated member and the support structure wherein the reaction axis is interposed between the first guide assembly and the second guide assembly. In this manner, the elongated member is guided in the support structure to minimize backlash.

BRIEF DESCRIPTION OF THE DRAWINGS

FIG. 5 is an exploded perspective view of the force actuator.

FIG. 7 is a schematic representation of the material testing system.

DETAILED DESCRIPTION OF THE PREFERRED EMBODIMENTS

Figure 1:
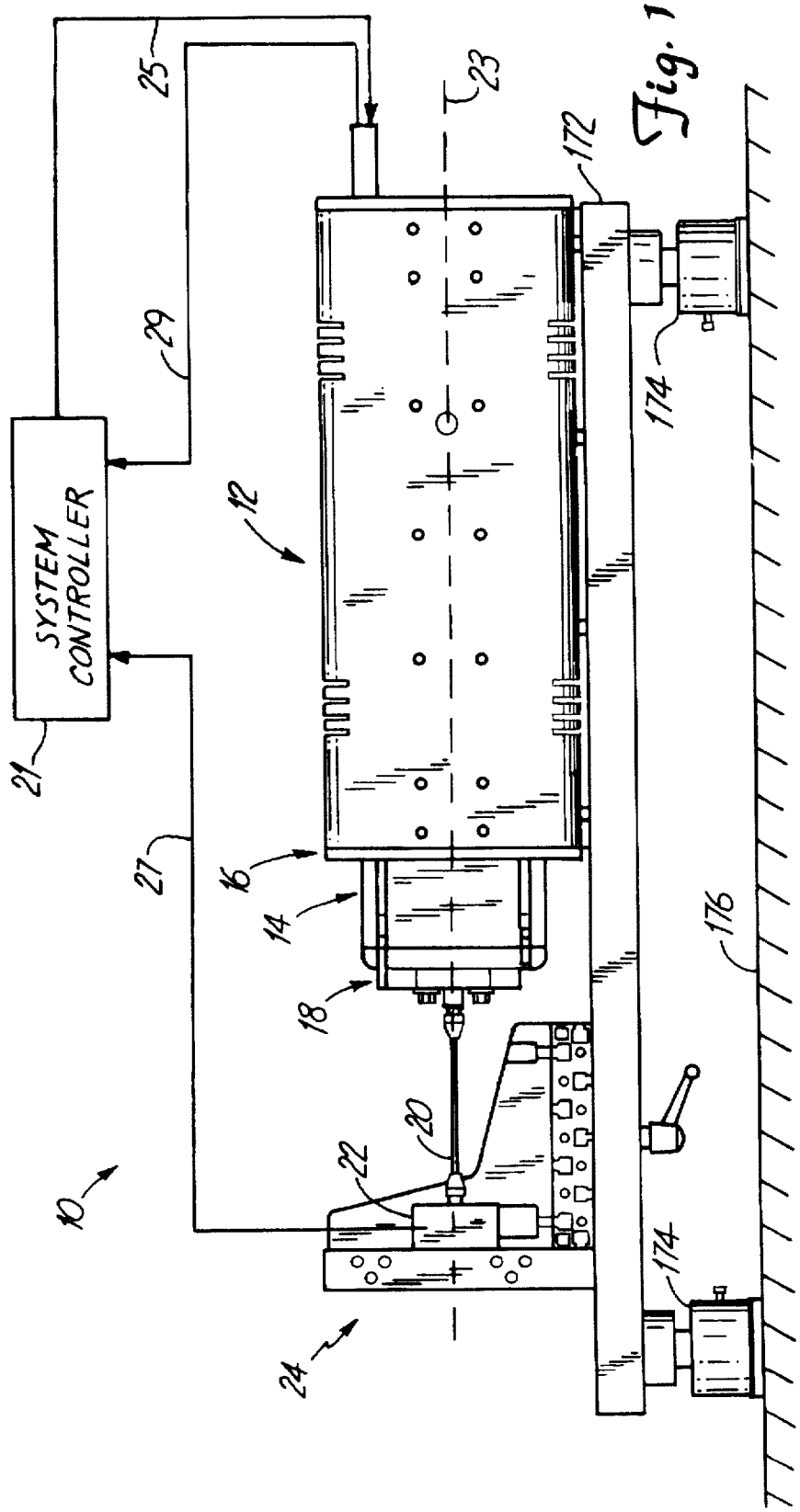
FIG. 1 is a side elevational view of a force actuator of the present invention coupled to a test specimen and secured to a support table.

FIG. 1 illustrates a material testing system 10 including a force actuator 12 of the present invention. The force actuator 12 includes a direct current (DC) brushless linear motor having an elongated member 14 linearly displaceable in a support structure 16. An end 18 of the elongated member 14 is coupled to a test specimen 20 to apply a force thereto. In one embodiment, an end of the test specimen 20 opposite the force actuator 12 is coupled to a load cell 22 that in turn is secured to a reaction structure 24. A system controller 21 energizes windings of the DC brushless linear motor through a power line 25 to generate an axial force upon the test specimen 20. Feedback signals from the load cell 22 on signal line 27 and/or signal lines represented at 29 from position sensors located in the support structure 16 are used by the system controller 21 to operate the DC brushless linear motor. The DC brushless motor of the force actuator 12 provides precision control capability and improved dynamic range previously unavailable from other prior art force actuators.

The force actuator 12 applies forces to the test specimen 20 along a test or reaction axis 23 that extends through the force actuator 12. Referring also to FIGS. 2–6, the elongated member 14 includes a coil assembly 26 that is guided within a housing 28 along the reaction axis 23. Two sets of permanent magnets 30A and 30B are secured to support plates 33A and 33B, which in turn, are secured to inner walls 32A and 32B, respectively, of the housing 28 along lines 31A and 31B that are equally spaced from and parallel to the reaction axis 23. The sets of permanent magnets 30A and 30B face the coil assembly 26 and are located on opposite sides of the reaction axis 23 in order that forces generated between the coil assembly 26 and the magnets 30A and 30B are balanced with respect to the reaction axis 23. In other words, the magnets 30A and 30B are symmetrically disposed about the reaction axis 23. Preferably, the elongated member 14 includes guide assemblies 34A and 34B that are also disposed on opposite sides of the reaction axis 23. Each guide assembly 34A and 34B includes a guide axis 35A and 35B, respectively. The guide axes 35A and 35B are spaced-apart and parallel to the reaction axis 23. In the embodiment illustrated, the guide axes 35A and 35B are equally spaced-apart from the reaction axis 23 and are disposed in a common plane with the reaction axis 23 in order to also balance forces on opposite sides of the elongated member 14.

Referring to FIG. 5, the elongated member 14 includes the coil assembly 26, a support panel 38 and an end mounting bar 40. The coil assembly 26 includes an upper mounting rail 42, a lower mounting rail 44 and a planar section 46 extending between the upper mounting rail 42 and the lower mounting rail 44. Opposed surfaces 48A and 48B (FIG. 6) of the planar section 46 face the sets of permanent magnets 30A and 30B, respectively. The coil assembly 26 includes windings forming a stator assembly 43 in the planar section 46. The coil assembly 26 includes suitable sensors such as Linear Hall Effect Devices, not shown, that provide output signals to the system controller 21 (FIG. 1) for motor commutation. The permanent magnets 30A and 30B and the coil assembly 26 are available from Trilogy Systems Corp. of Webster, Tex.

The support panel 38 is secured to an end of the coil assembly 26 and extends out of the housing 28 when the elongated member 14 is mounted therein. The support panel 38 is formed of a suitable material, for example an epoxied graphite panel, that can withstand the forces generated and applied to the test specimen 20.

A channel 50 formed in the end mounting bar 40 receives an end 52 of the support panel 38. The end mounting bar 40 includes an adjustable coupling indicated at 54. In the embodiment illustrated, the adjustable coupling 54 includes a "T-shaped" channel 56 that receives a slidable assembly 58. Fasteners 60 selectively hold the assembly 58 at a desired position within the channel 56.

Figure 6:
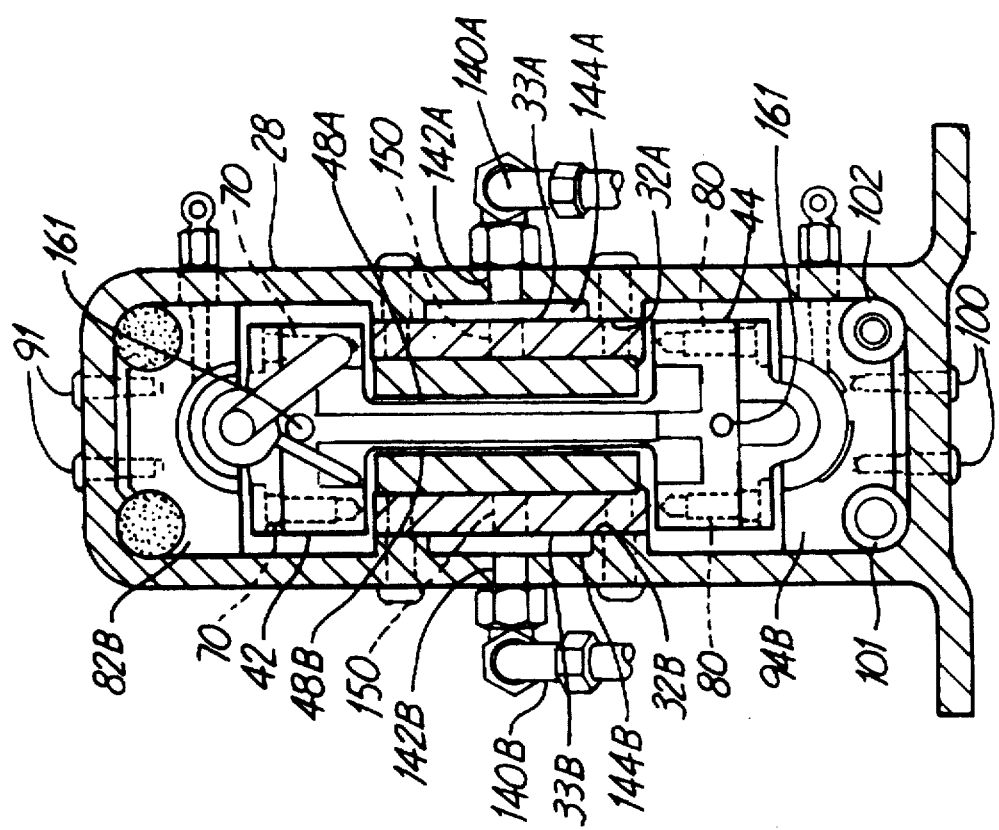
FIG. 6 is a sectional view of the force actuator taken along lines 6—6 in FIG. 2.
Figure 3:
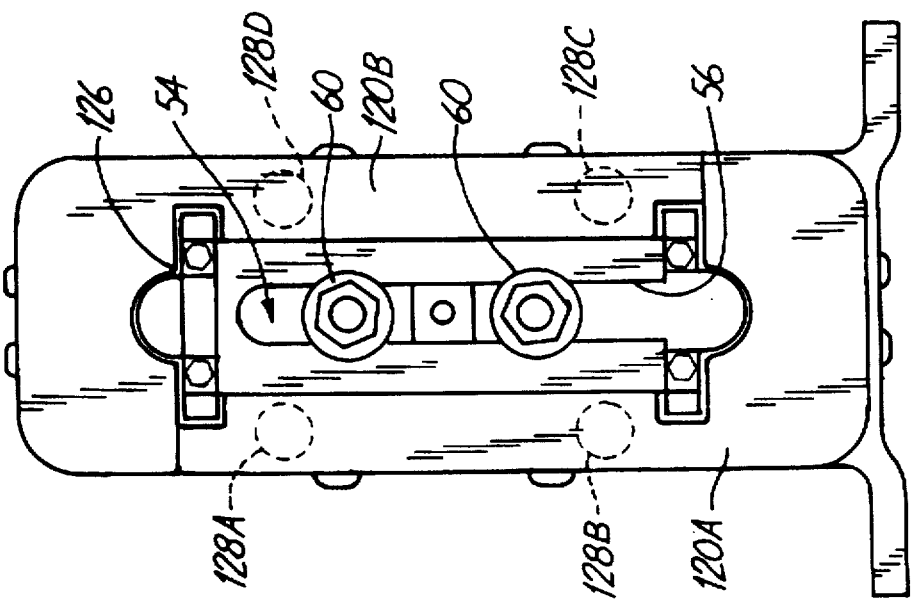
FIG. 3 is a front plan view of the force actuator.

Longitudinal guide rails 62A and 62B extend from the end mounting bar 40 to a remote end of the coil assembly 26 on opposite sides of the reaction axis 23 and form part of the guide assemblies 34A and 34B, respectively. The guide rail 62A includes a mounting surface 64 and a longitudinal channel 66 opening to the mounting surface 64. The channel 66 receives a portion 68 of the support panel 38 extending parallel to the reaction axis 23, while the mounting surface 64 is secured to the upper mounting rail 42 of the coil assembly 26 with bolts, two of which are illustrated in FIG. 6 at 70. Bolts 72 secure the end mounting bar 40 to the guide rail 62A.

The guide rail 62B is similarly constructed having a mounting surface 74 and a longitudinal channel 76. The longitudinal channel 76 receives a portion 78 of the support panel 38 and is similarly attached to the coil assembly 26 and the end mounting bar 40 with bolts 80 (FIG. 6) and bolts 82, respectively. Preferably, the support panel 38 is joined to the coil assembly 26, the end mounting bar 40 and the guide rails 62A and 62B with a suitable epoxy. A fixture, not shown, can be used to assure proper alignment of the components.

The elongated member 14 is supported in the housing 28 with the guide assemblies 34A and 34B. In the embodiment illustrated, the guide assembly 34A includes spaced-apart air bearings 82A and 82B, for example, available from New Way Machine Components Inc. of Aston, Pa. The air bearings 82A and 82B each have a channel 86 formed in a porous carbon substrate 88. The substrate 88 is mounted to a carriage 89. Pressurized air from an air source 90 (FIG. 4) through an aperture 92 in each carriage 89. The aperture 92 opens to the substrate 88 diffuses through the substrate 88 providing a constant pressure profile across a bearing face 88A of the substrate 88. Air bearings 94A and 94B are identical to the air bearings 82A and 82B, and are operably coupled to the guide rail 62B. An outer surface of each guide rail 62A and 62B is formed so as to correspond with the bearing face of the air bearings 82A, 82B, 94A and 94B.

Mounting assemblies 93A and 93B allow limited movement of the air bearings 82A and 82B to compensate for thermal expansion of the elongated member 14. In the embodiment illustrated, floating retaining screws 91 secure the air bearings 82A and 82B to the housing 28. Preferably, a compliant mounting member is provided between the air bearings 82A and 82B and the housing 28. In the embodiment illustrated, the compliant mounting member comprises two rubber rods 96A and 96B. Each of the air bearings 82A and 82B include recesses 98 that receive the rubber rods 96A and 96B.

The air bearings 94A and 94B are secured rigidly to the housing 28 with fasteners 100. In view that the air bearings 94A and 94B are identical to the air bearings 82A and 82B, a spacer tube or rod 101 is provided. The rod 101 has a diameter similar to the rubber rods 96A and 96B.

Figure 2:
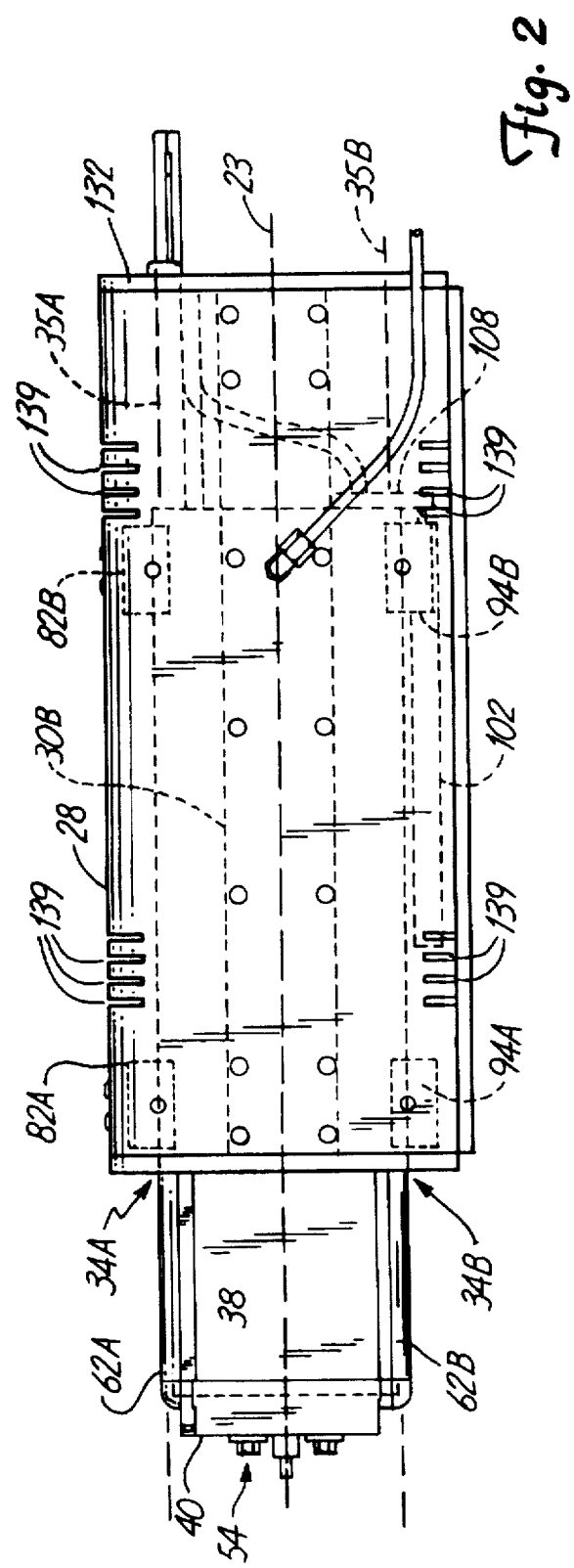
FIG. 2 is a side elevational view of the force actuator.

Referring to FIGS. 2 and 5, a sensor 102 measures displacement of the elongated member 14 with respect to the housing 28. In the embodiment illustrated, the sensor 102 comprises an LVDT displacement sensor. The LVDT sensor includes an inner rod 104 having an end 106 that is coupled to a plate 108. The plate 108 is attached to an end of the coil assembly 26. The inner rod 104 moves longitudinally through an aperture of an outer housing 110, which is secured to the housing 28. An outer diameter of the outer housing 110 is similar to the rubber rods 96A and 96B so as to be disposed between the air bearing 94B and the housing 28.

Plate members 120A and 120B are securable to an end surface 122 of the housing 28 and together form an aperture 126 (FIG. 3) suitable for the elongated member 14. Compliant pads 128A, 128B, 128C and 128D are secured to the plate members 120A and 120B. Corresponding surface portions 130 of the elongated member 14 contact the compliant members 128A, 128B, 128C and 128D, respectively, when the elongated member 14 has reached the end of its stroke. An end plate 132 mounted to an end surface of the housing 28 also includes compliant pads 134A, 134B, 134C and 134D that provide cushioned stops when the elongated member 14 is fully retracted within the housing 28.

Figure 4:
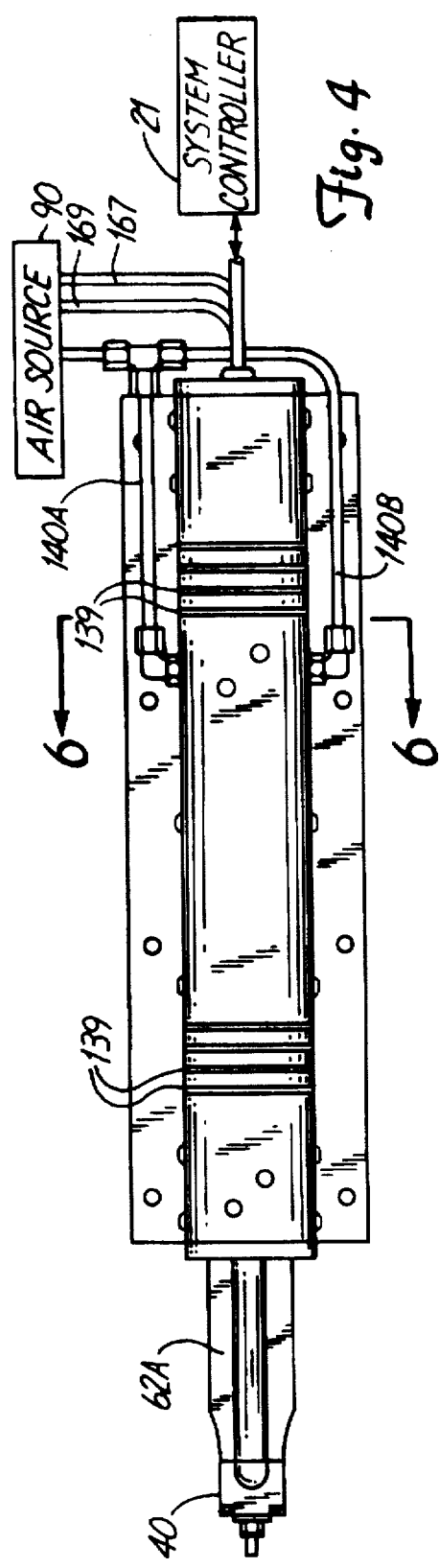
FIG. 4 is a top plan view of the force actuator.

In the embodiment illustrated, a cooling fluid circulates within the housing 28 and out through slots 139 to cool the magnets 30A and 30B and the coil assembly 26. Preferably, the cooling fluid is a gas such as air provided from the air source 90. Referring to FIGS. 4 and 6, lines 140A and 140B couple the air source 90 to ports 142A and 142B provided on opposite sides of the housing 28. The ports 142A and 142B each open to fluid passageways 144A and 144B provided between the support plates 33A and 33B and the housing 28. Air cooling ports 150 are provided in each of the support plates 33A and 33B between gaps 143 (FIG. 5) formed between the magnets to fluidly communicate with the passageways 144A and 144B.

Referring back to FIG. 5, separate passageways, such as illustrated at 153 in the upper mounting rail 42, are formed in the upper mounting rail 42 and the lower mounting rail 44 to provide additional cooling. Each of the mounting rails 42 and 44 includes apertures 155 that face opposed inner surfaces of the housing 28, and apertures 157 that face each other to provide cooling fluid directly on the magnets 30A and 30B and along the surfaces 48A and 48B. Using the passageway 153 in the upper mounting rail 42 and the apertures 157 illustrated in the lower mounting rail 44 by way of example, each passageway includes a longitudinal center passageway 159 and horizontal branch passageways 161 extending therefrom that open to one of the apertures 155. Individual vertical passageways 163 are fluidly coupled to each of the horizontal passageways 161 and open to one of the apertures 157. Separate air lines 167 and 169 are fluidly coupled to each of the center passageways 161 in the mounting rails 42 and 44, respectively, and extend out through an aperture 171 in the end plate 132. The lines 167 and 169 are coupled to the air source 90.

Referring back to FIG. 1, the force actuator 12 is adjustably fixed to a support base 172. Air adjustable isolator mounts 174 isolate the support base 172 from a support surface 176 and allow the support base 172 to be leveled.

A conventional DC brushless linear motor is illustrated in FIG. 7. As is known to the skilled artisan, the DC brushless linear motor includes a motor drive 178 having a rectifier 180 receiving a suitable alternating current input signal on signal lines 182 to produce fixed positive, and negative DC voltages on a positive bus 184 and a negative bus 186, respectively. A capacitor 188 is provided to maintain the positive bus 184 and the negative bus 186 within the suitable limits. An inverter 190, for example, a three phase inverter, is connected to the positive bus 184 and the negative bus 186 in a conventional manner to provide commutated current wave forms on power signal lines 192A, 192B and 192C, which are connected to the stator windings 43 of the coil assembly 26. The inverter 190 includes power transistors 191 for switching each of the signal lines 192A–192C from an open circuit condition to the positive bus 184 or the negative bus 186. The duty cycle of each transistor 191 is controlled by an inverter driver 194, which can be a logic array stored in read only memory (ROM). The logic array stored in ROM responds to feedback signals provided from the Linear Hall Effect Devices 193 to indicate the position of the elongated member 14. Suitable motor drives are available from Western Servo Design, Inc. of Fremont, Calif.

In the embodiment illustrated, the system controller 21 includes a computer 200 connected to the motor drive 178. A program executed by the computer 200 generates suitable command signals for the motor drive 178 in order to apply desired load profiles to the test specimen 20. The computer 200 receives feedback signals from the LVDT sensor 102 and/or feedback signals from the load cell 22. A suitable computer and software (Test Star II™) programs are available from MTS Systems Corporation of Eden Prairie, Minn. Due to the servo control of the system 10, there are no discrete steps, but rather, continuous positioning of the elongated member 14 relative to the support structure 16.

Although the present invention has been described with reference to preferred embodiments, workers skilled in the art will recognize that changes may be made in form and detail without departing from the spirit and scope of the invention.

What is claimed is:

1. A material testing machine comprising:

a support structure;

a DC brushless linear motor operable to develop a force along a reaction axis, the DC brushless linear motor comprising:

a first set of magnets disposed along a first line on the support structure parallel to the reaction axis;

a second set of magnets disposed along a second line on the support structure parallel to the first line, wherein the second set of magnets face the first set of magnets and wherein the reaction axis is interposed between the first line and the second line;

an elongated member guided on the support structure, the elongated member being disposed on the reaction axis;

a plurality of coils disposed on the elongated member proximate the first set of magnets and the second set of magnets;

a controller for selectively energizing the coils;

a coupling member coupleable to a specimen to be tested, the coupling member being disposed on an end of the elongated member and coupleable to specimen to be tested wherein the reaction axis extends through the coupling member;

a first guide assembly operably connected between the support structure and the elongated member and having a first guide axis spaced-apart and parallel to the reaction axis; and a second guide assembly operably connected between the support structure and the elongated member and having a second guide axis spaced-apart and parallel to the reaction axis.

2. The material testing machine of claim 1 wherein the first guide axis, the second guide axis and the reaction axis are disposed in a common plane.

3. The material testing machine of claim 1 and a mounting assembly mounting one of the guide assemblies to the support structure, the mounting assembly allowing limited movement of the guide assembly relative to the support structure.

4. The material testing machine of claim 2 wherein the first guide assembly and the second guide assembly comprise air bearings.

5. The material testing machine of claim 4 and a mounting assembly mounting one of the guide assemblies to the support structure, the mounting assembly allowing limited movement of the guide assembly relative to the support structure.

6. The material testing machine of claim 3 wherein the mounting assembly includes a compliant member disposed between the elongated member and the support structure.

7. The material testing machine of claim 5 wherein the mounting assembly includes a compliant member disposed between the elongated member and the support structure.

8. The material testing machine of claim 1 and further comprising a fluid source fluidly coupled to cooling passageways provided in the support structure.

9. The material testing machine of claim 2 wherein the fluid source comprises a source of gas and wherein the passageways open proximate the magnets.

* * * * *

UNITED STATES PATENT AND TRADEMARK OFFICE
CERTIFICATE OF CORRECTION

PATENT NO.  : 5,767,402
DATED       : June 16, 1998
INVENTOR(S) : Sandlass et al.

It is certified that error appears in the above-identified patent and that said Letters Patent is hereby corrected as shown below:

Column 8, line 7, replace "2" with --8--.

Signed and Sealed this

Ninth Day of March, 1999

Attest:

Q. TODD DICKINSON

*Attesting Officer*        *Acting Commissioner of Patents and Trademarks*